(12) United States Patent
Jansheski et al.

(10) Patent No.: US 7,997,287 B2
(45) Date of Patent: Aug. 16, 2011

(54) DENTAL FLOSSER WITH TONGUE CLEANER

(75) Inventors: John M. Jansheski, Maryville, TN (US); Lex Shankle, Maryville, TN (US)

(73) Assignee: Dentek Oral Care, Inc., Maryville, TN (US)

( * ) Notice: Subject to any disclaimer, the term of this patent is extended or adjusted under 35 U.S.C. 154(b) by 206 days.

(21) Appl. No.: 11/671,561

(22) Filed: Feb. 6, 2007

(65) Prior Publication Data
US 2008/0185016 A1 Aug. 7, 2008

(51) Int. Cl.
*A61C 15/00* (2006.01)
(52) U.S. Cl. .......................... 132/323; 132/329
(58) Field of Classification Search .................. 132/321, 132/309, 329, 323; D28/64, 57, 68, 65, 66
See application file for complete search history.

(56) References Cited

U.S. PATENT DOCUMENTS

| | | | |
|---|---|---|---|
| 1,658,706 A * | 2/1928 | Carrott | 132/309 |
| 2,233,936 A | 3/1941 | Campbell | |
| 2,444,638 A * | 7/1948 | Dobbins | 132/324 |
| 3,779,256 A * | 12/1973 | Maloney et al. | 132/329 |
| D274,375 S | 6/1984 | Tomlin | |
| D276,088 S * | 10/1984 | Fong | D28/68 |
| D309,041 S | 7/1990 | Schneider | |
| D316,617 S | 4/1991 | Cheung | |
| 5,246,021 A | 9/1993 | Katz | |
| D348,332 S | 6/1994 | Haggett-King et al. | |
| D382,367 S | 8/1997 | Andrade et al. | |
| 5,704,379 A * | 1/1998 | Krynicki | 132/323 |
| D403,120 S | 12/1998 | Enriquez | |
| D412,043 S | 7/1999 | Dolan et al. | |
| D424,748 S * | 5/2000 | Dolan et al. | D28/68 |
| 6,083,235 A | 7/2000 | Wagner | |
| 6,092,536 A * | 7/2000 | Owens | 132/325 |
| D441,142 S | 4/2001 | Doyscher | |
| 6,352,545 B1 | 3/2002 | Wagner | |
| D463,626 S * | 9/2002 | Huang | D28/65 |
| D481,829 S | 11/2003 | Gwen | |
| D484,643 S | 12/2003 | Nanda | |
| D489,490 S | 5/2004 | Chodorow | |
| 2004/0035440 A1 | 2/2004 | Cheng | |
| 2004/0040572 A1 | 3/2004 | Chodorow | |
| 2005/0133058 A1 | 6/2005 | Ding | |

FOREIGN PATENT DOCUMENTS

| | | |
|---|---|---|
| GB | 202439 | 5/1922 |
| JP | 7100153 | 4/1995 |

* cited by examiner

*Primary Examiner* — Robyn Doan
(74) *Attorney, Agent, or Firm* — Luedeka, Neely & Graham, PC

(57) ABSTRACT

A dental flosser having a tongue cleaner, the flosser including a handle terminating at a head: a pair of spaced apart arms extending from the head; a length of dental floss extending between the arms; and a rugous surface on at least one of the arms suitable for being scraped against the tongue of a user for effectively cleaning the tongue.

12 Claims, 4 Drawing Sheets

DENTAL FLOSSER WITH TONGUE CLEANER

FIELD

This disclosure relates to the field of dental flossers. More particularly, this disclosure relates to a dental flosser which includes structure thereon useful for cleaning the tongue of a user.

BACKGROUND

Regular flossing and cleaning of the teeth and mouth are important for dental health. Disposable dental flossers are widely available and are useful for flossing. However, beyond flossing, it is recognized that halitosis and other dental concerns may be helped by scraping or otherwise cleaning the tongue. However, while disposable dental flossers are widely available, they are not effective for cleaning the tongue. What is desired is a dental flosser, particularly a disposable dental flosser, which is also effective for cleaning the tongue.

SUMMARY

The above and other needs are met by a dental flosser having a tongue cleaner.

In a preferred embodiment, the flosser includes a handle terminating at a head; a pair of spaced apart arms extending from the head; a length of dental floss extending between the arms; and a rugous surface on at least one of the arms suitable for being scraped against the tongue of a user for effectively cleaning the tongue.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
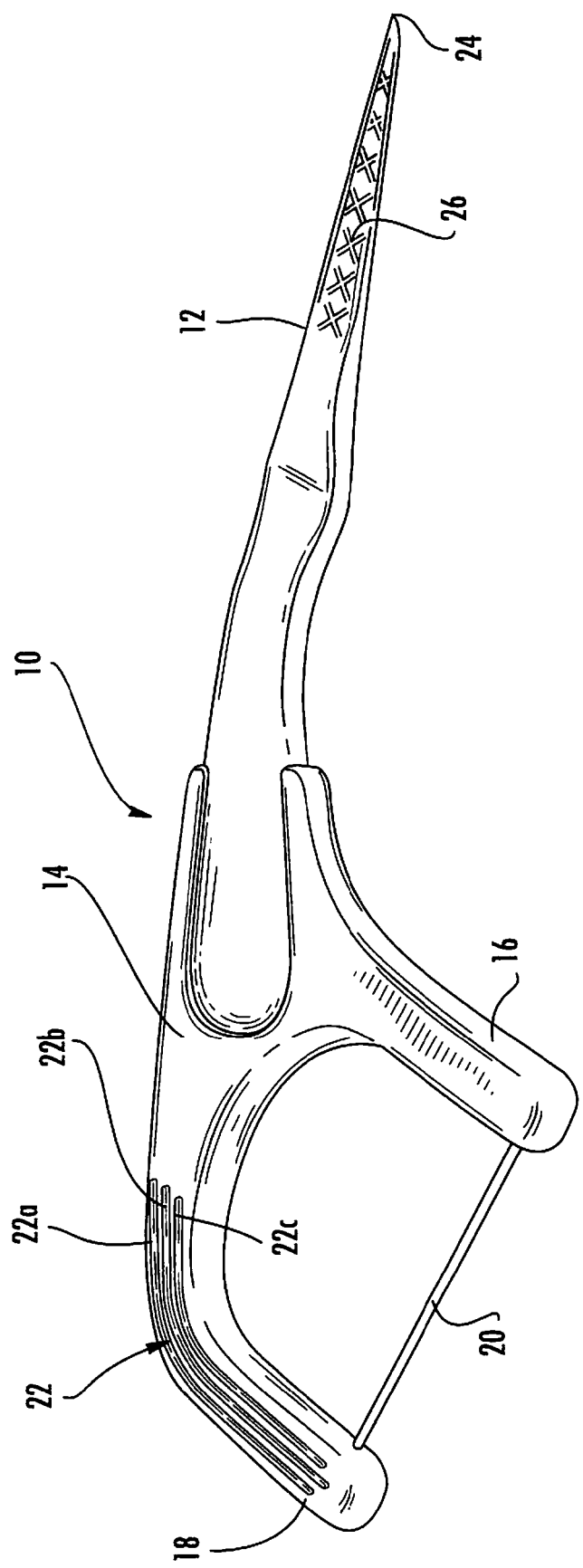
FIG. 1 is a perspective view of a dental flosser having a tongue cleaner according to an embodiment of the disclosure.
Figure 2:
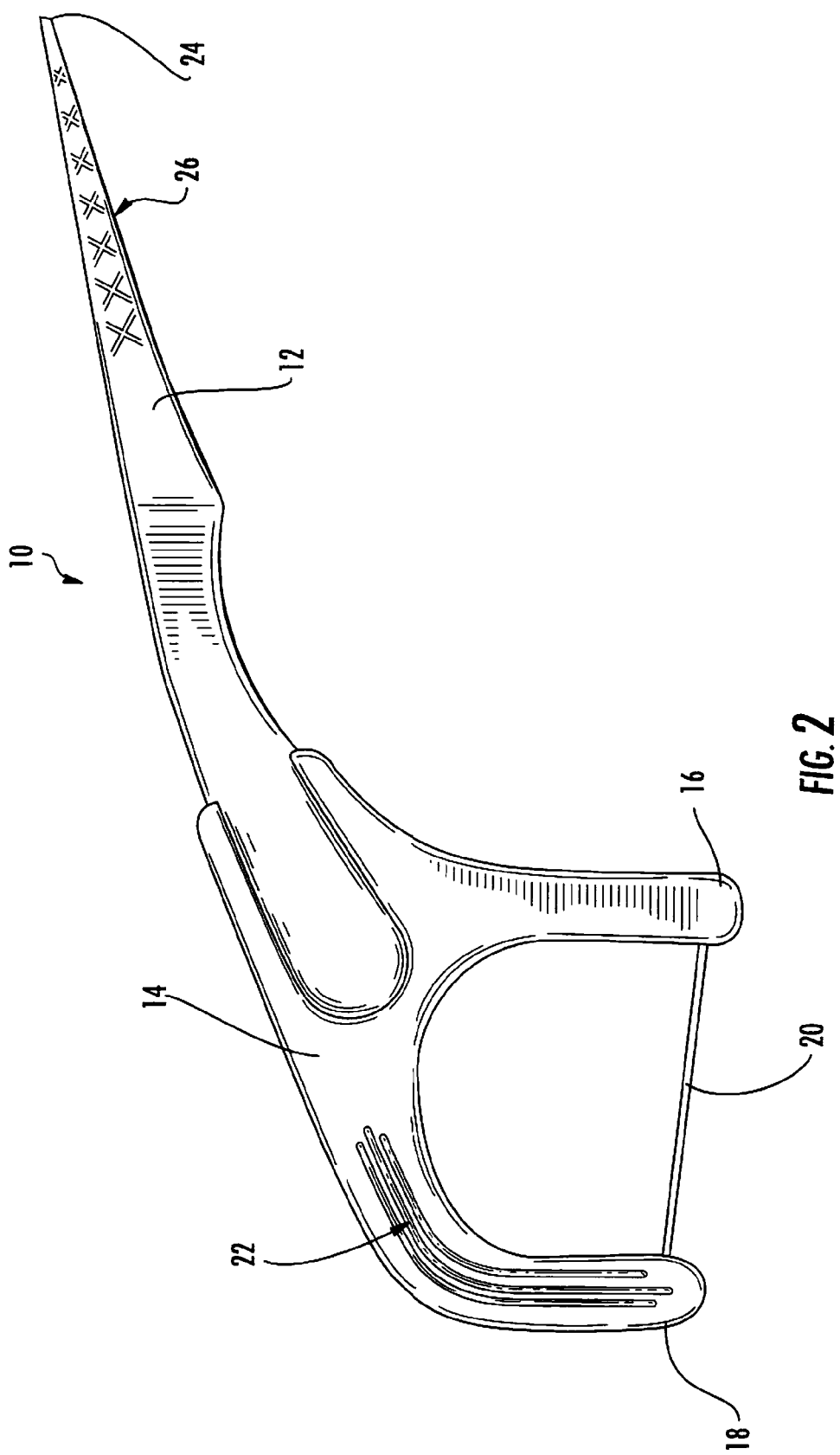
FIG. 2 is a top plan view of the flosser of FIG. 1.
Figure 3:
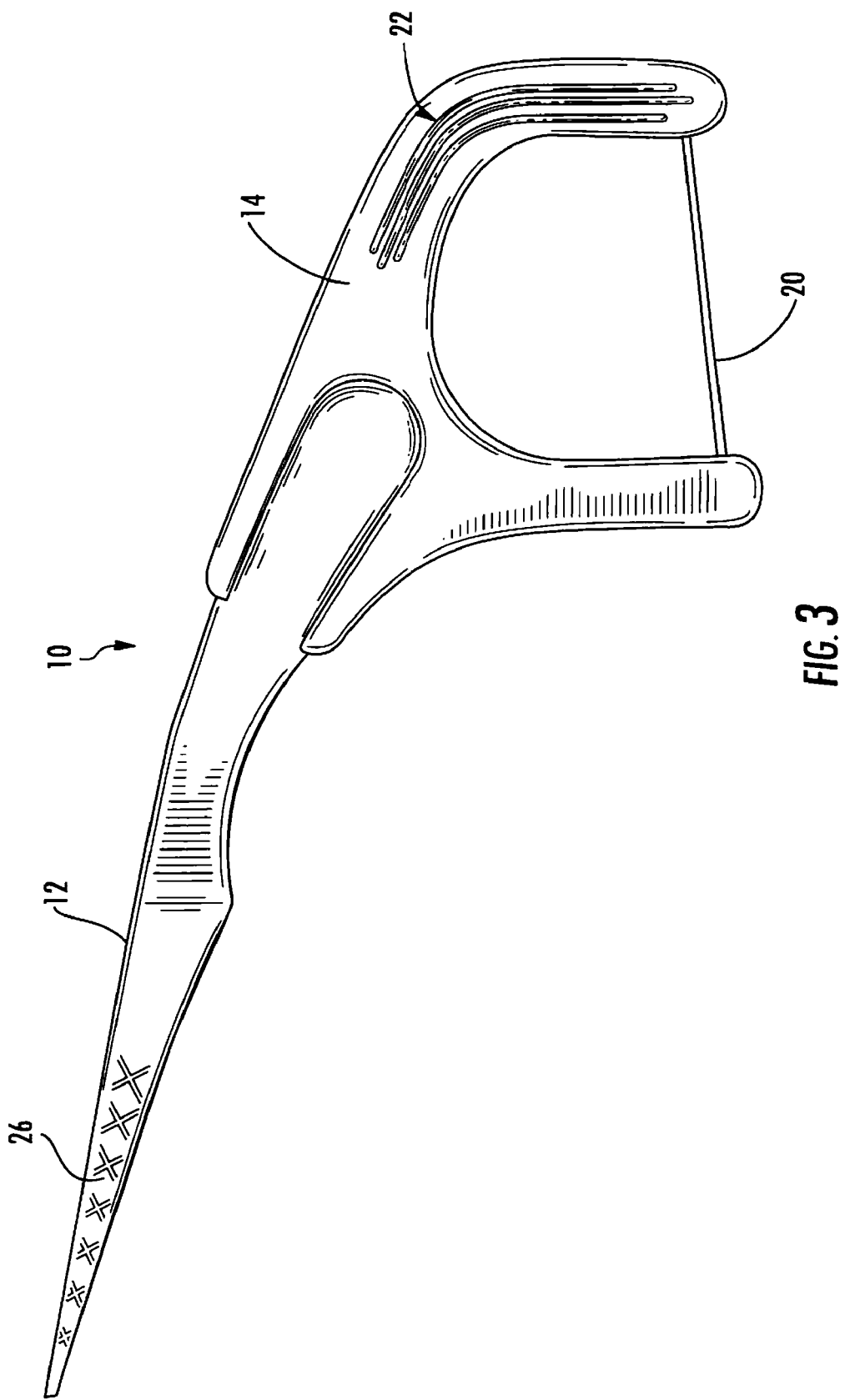
FIG. 3 is a bottom plan view of the flosser of FIG. 1.

With reference to the drawings, the disclosure relates to a dental flosser 10 having a handle 12 terminating at a head 14. A pair of spaced apart arms 16 and 18 extend from the head 14. The arms are shown oriented substantially parallel to one another, but it will be understood that they may be otherwise oriented so as to provide spaced apart ends for supporting dental floss. A length of dental floss 20 extends between the arms 16 and 18.

To provide structure useful for cleaning the tongue, a rugous tongue cleaning surface 22, provided for example by a plurality of elongate and spaced apart raised ribs 22a-22c, is defined on a surface of the arm 18 and also preferably a portion of the head 14. To clean the tongue, a user may extend his tongue, place the tongue cleaning surface 22 at the back of the tongue, and pull forward skinning the surface of the tongue. If desired, either additionally or alternatively, a rugous tongue cleaning surface corresponding to the surface 22 may be provided on the arm 16 in a similar manner. Also, it will be understood that the tongue cleaning surface 22 may be provided on one or both sides of the arm 16 or the arm 18.

The end of the handle 12 opposite the head 14 is preferably tapered to provide a pick end 24. The pick end 24 may have a rugous cleaning surface 26 on one or both sides thereof. The cleaning surface 26 is a roughened or rugous cleaning surface provided as by a textured pattern provided during the molding process configured to facilitate the removal of food particles and to stimulate the gums. For example, the user may place the pick end 24 between the teeth and gently press against the gum, supplying an in and out motion to remove food particles and stimulate the gums.

As will be appreciated, an advantage of the structure described herein is that it is relatively compact and provides supplemental cleaning surfaces on existing surfaces of the flosser.

The flosser 10 is preferably a disposable flosser made of one-piece molded plastic construction, with the rugous cleaning surfaces being formed during the molding process. The floss 20 is permanently attached to the arms 16 and 18 in the molding process. To floss the teeth, the user may position the floss 20 between the teeth and gently slide the floss up and down, allowing the floss to wrap around the teeth, cleaning above and below the gum line.

Figure 4:
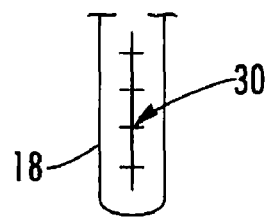
FIGS. 4-7 show alternate embodiments of tongue cleaning structure for use with the flosser of FIG. 1.
Figure 5:
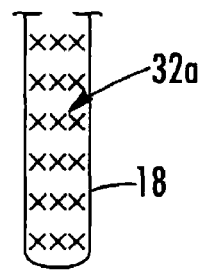
Figure 6:
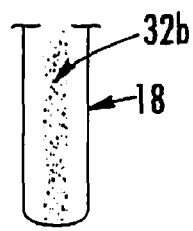
Figure 7:
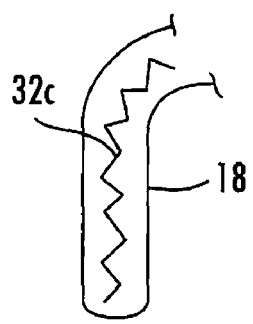

The ribs 22 are each provided during the molding process and may be of uniform or non-uniform height, length, and width. It will be further understood that the ribs 22a-22c may be provided in various patterns and numbers. For example, a single rib 30 has been observed to provide structure sufficient for tongue cleaning purposes when configured as shown in FIG. 4. Other examples of configurations of rugous surfaces 32a-32c suitable for tongue cleaning purposes are shown in FIGS. 5-7.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A dental flosser having a tongue cleaner, the flosser comprising:
    a handle terminating at a head, where the handle further includes a tapered pick end opposite the head having a rugous cleaning surface on at least one side thereof;
    a pair of spaced apart arms extending from the head, the spaced apart arms having a first end and a second end, the first end of the spaced apart arms adjoining the head of the handle;
    a length of dental floss extending between the second end of the arms; and
    a first rugous tongue cleaning surface defined on at least one of the arms between the first end and the second end.
2. The flosser of claim 1, wherein the first rugous tongue cleaning surface comprises a plurality of elongate and spaced apart raised ribs defined on a surface of the arm and a portion of the head.

3. The flosser of claim 1, further comprising a second rugous tongue cleaning surface on a portion of the arm opposite the first rugous tongue cleaning surface.

4. The flosser of claim 1, wherein the dental flosser is of one-piece molded plastic construction and the rugous cleaning surfaces are provided during the molding process.

5. The flosser of claim 1 wherein the first rugous tongue cleaning surface comprises at least one elongate and spaced apart raised rib defined on a surface of the arm and a portion of the head.

6. A dental flosser, the flosser comprising:
  a handle terminating at a head;
  a pair of spaced apart arms extending from the head, the spaced apart arms having a first end and a second end, the first end of the spaced apart arms adjoining the head of the handle;
  a tongue cleaning surface defined on at least one of the spaced apart arms between the first end and the second end;
  a length of dental floss extending between the second end of the arms;
  a tapered pick end defined on an end of the handle opposite the head; and
  a rugous cleaning surface defined on at least one side of the tapered pick end.

7. The flosser of claim 6, wherein the dental flosser is of one-piece molded plastic construction and the rugous cleaning surface is a textured pattern provided during the molding process configured to facilitate the removal of food particles and to stimulate the gums.

8. A dental flosser having a tongue cleaner, the flosser comprising:
  a handle terminating at a head, where the handle further includes a tapered pick end opposite the head having a rugous cleaning surface on at least one side thereof;
  a pair of spaced apart arms extending from the head, the spaced apart arms having a first end and a second end, the first end of the spaced apart arms adjoining the head of the handle;
  a tongue cleaning surfaces defined on both of the spaced apart arms between the first end and the second end of the arms; and
  a length of dental floss extending between the second end of the arms.

9. A method of tongue cleaning, the method comprising:
  placing a dental flosser in a mouth of a user, the dental flosser having a handle terminating at a head, a pair of spaced apart arms extending from the head, the spaced apart arms having a first end and a second end, the first end of the spaced apart arms adjoining the head of the handle, and a length of dental floss extending between the second end of the arms;
  cleaning the tongue with a first rugous tongue cleaning surface defined on at least one of the arms between the first end and the second end.

10. The method of claim 9 further comprising flossing between one or more teeth of the user using the dental flosser.

11. The method of claim 9 wherein the first rugous tongue cleaning surface comprises at least one elongate and spaced apart raised rib defined on a surface of the arm and a portion of the head.

12. The method of claim 9 wherein cleaning the tongue further comprises cleaning the tongue with a second rugous tongue cleaning surface on a portion of the arm opposite the first rugous tongue cleaning surface.

* * * * *